(12) United States Patent
Gorsek

(10) Patent No.: US 6,383,482 B1
(45) Date of Patent: May 7, 2002

(54) WEIGHT LOSS COMPOSITION CONTAINING GREEN TEA, HYDROXYCITRIC ACID, 5-HYDROXYTRYPTOPHAN, GLUCOMANNAN, PICOLINATE AND *LACTOBACILLUS*

(75) Inventor: Wayne F. Gorsek, Springfield, IL (US)

(73) Assignee: Vitacost.Com, Inc., Boynton Beach, FL (US)

( * ) Notice: Subject to any disclaimer, the term of this patent is extended or adjusted under 35 U.S.C. 154(b) by 0 days.

(21) Appl. No.: 09/643,678

(22) Filed: Aug. 24, 2000

(51) Int. Cl.[7] ........................ A61K 35/78; A61K 38/43; A01N 63/02

(52) U.S. Cl. .................... 424/93.45; 424/729; 424/626; 424/94.1

(58) Field of Search .............................. 424/93.45, 729, 424/626, 94.1

(56) References Cited

U.S. PATENT DOCUMENTS 5,164,384 A * 11/1992 Paul
5,626,849 A * 5/1997 Hatings et al.
5,795,576 A * 8/1998 Diaz et al.
6,207,699 B1 * 3/2001 Rothman

FOREIGN PATENT DOCUMENTS

FR 2746648 A1 * 10/1997
JP 406343419 A * 12/1994

* cited by examiner

Primary Examiner—Christopher R. Tate
Assistant Examiner—Mike Meller
(74) Attorney, Agent, or Firm—Hoffman, Wasson & Gitler, PC

(57) ABSTRACT

A powerful formulation for weight loss containing green tea extract, hydroxycitric acid, 5-hydroxytryptophan, glucomannan, chromium picolinate, and *Lactobacillus acidophilus* is disclosed. The formulation boasts metabolic rates, suppresses appetite and helps burn fat.

2 Claims, No Drawings

WEIGHT LOSS COMPOSITION CONTAINING GREEN TEA, HYDROXYCITRIC ACID, 5-HYDROXYTRYPTOPHAN, GLUCOMANNAN, PICOLINATE AND LACTOBACILLUS

BACKGROUND OF THE INVENTION

The invention relates to a composition for permanent weight management. The composition burns fat, boost metabolic rate, controls appetite, eliminates sugar cravings and eating binges. An orally ingested composition is provided which contains effective amounts of vitamins, minerals, herbs and natural extracts. The composition contains no dangerous stimulants like Ephedrine, commonly known as Ma Huang.

The process by which weight is controlled is so complex that even most talented scientists do not understand it.

Prior formulations such as those disclosed in U.S. Pat. No. 5,626,849 fall short of the unique blend which requires 5-hydroxytryptophan as a key nutrient to provide a feeling of satiation and a calming effect for healthy weight management.

It is an object of the present invention to provide an unique formulation which allows individuals to lose weight and keep it off.

SUMMARY OF THE INVENTION

The key to the unique formulation is a combination of specific vitamins, minerals, herbs and nutrients. These essential components not only burn fat and boost metabolic rate, but they control appetite, eliminate sugar cravings, eating binges and more.

The formulation contains green tea extract, hydroxycitric acid, 5-hydroxytryptophan (5-HTP), glucomannen, chromium picolinate, and a lactobacillus.

The formulation is preferably delivered in capsule form at 6 capsules per day.

DETAILED DESCRIPTION OF THE INVENTION

The present invention involves a composition for oral ingestion that contains standardized green tea extract, hydroxycitric acid, 5-hydroxytryptophan, glucomannen, chromium percolinate, lactobacillus and other minor nutrients. More specifically, this formulated product is a permanent weight management composition. This product allows for excess fat to be burned, metabolic rates to be boosted, appetite to be controlled, eating binges to be curtained and for the elimination of sugar cravings.

In order to secure the desired result the following essential components are provided:

Standardized Green tea extract (standardized for 20% polyphenols) (leaf), approximately 200 mg, the component inhibits the enzyme that causes the breakdown of norepinephrine, thus causing an increase in metabolic rate. It has also been shown to increase the rate of brown fat metabolism.

Hydroxycitric acid, a rare organic acid, reduces appetite and helps prevent excess carbohydrates from being stored as body fat. (Approximately 1500 mg (1.5 g))

5-hydroxytryptophan, a precursor to seratonin, is an effective nutrient that promotes weight loss. The component gives the feeling of satiation and a calming effect. (200 mg)

Glucomannen is a natural calorie free, pectin like gel fiber which absorbs liquid (up to 50 times its weight) giving a feeling of fullness. (3000 mg (3 g))

Chromium picolinate, a mineral, helps insulin to metabolize fat, turns protein into muscle, and converts sugar into energy. (400 mcg)

*Lactobacillus acidophilus* helps balance the digestive system with friendly flora producing many key nutrients like biotin and vitamin K. It also helps inhibit the overgrowth of bad bacteria and yeast. By helping restore peak health to the digestive tract, this probiotic is another key component of the weight management system. The enzymes work with the digestive system to break down food into micronutrients and is more easily assimilated for optimum health and energy.

In addition to the key components, other components such as kosher gelatin (capsules), magnesium stearate and silicon dioxide are included.

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. A weight loss composition comprising effective amounts of:

green tea extract;

hydroxycitric acid;

5-hydroxytryptophan;

glucomannan;

chromium picolinate; and

*Lactobacillus acidophilus.*

2. A weight loss composition comprising:

200 mg green tea extract;

1500 mg hydroxycitric acid;

200 mg 5-hydroxytryptophan;

3000 mg glucomannan;

400 mcg chromium picolinate;

100 mg *lactobacillus acidophilus;* and 500 mg plant source enzymes.

* * * * *